United States Patent [19]

Shionozaki

[11] Patent Number: 4,518,226

[45] Date of Patent: May 21, 1985

[54] ESTER-AZOXY COMPOUNDS

[75] Inventor: Yoshio Shionozaki, Nagano, Japan

[73] Assignee: Kabushiki Kaisha Suwa Seikosha, Tokyo, Japan

[21] Appl. No.: 540,985

[22] Filed: Oct. 11, 1983

[30] Foreign Application Priority Data

Oct. 20, 1982 [JP] Japan ................. 57-185150

[51] Int. Cl.$^3$ .................. C09K 3/34; G02F 1/13; C07C 105/00
[52] U.S. Cl. .................. 350/350 R; 252/299.5; 252/299.63; 252/299.64; 252/299.68; 534/566; 350/350 S
[58] Field of Search ........... 252/299.5, 299.63, 299.64, 252/299.68; 350/350 R, 350 S; 260/143

[56] References Cited

U.S. PATENT DOCUMENTS

| 3,773,747 | 11/1973 | Steinstrasser | 252/299.68 |
| 4,002,670 | 1/1977 | Steinstrasser | 252/299.64 |
| 4,009,934 | 2/1977 | Goodwin et al. | 252/299.64 |
| 4,113,647 | 9/1978 | Coates et al. | 252/299.63 |
| 4,293,434 | 10/1981 | Deutscher et al. | 252/299.63 |

FOREIGN PATENT DOCUMENTS

| 65869 | 12/1982 | European Pat. Off. | 252/299.63 |
| 53-87986 | 8/1978 | Japan | 252/299.64 |

OTHER PUBLICATIONS

C.A., vol. 92:47674n (1980).
Gray, G. W., et al., Mol. Cryst. Liq. Cryst., vol. 53, pp. 147–166 (1979).
Hochapfel, A., et al., Mol. Cryst. Liq. Cryst., vol. 37, pp. 109–119 (1976).
de Jeu, W. H., et al., Philips Res. Repts., vol. 27, pp. 172–185 (1972).
Demus, D. et al., Flussige Kristalle in Tabellen, Veb Deutscher Verlag, Leipzig, pp. 170–172 (1974).

Primary Examiner—Teddy S. Gron
Attorney, Agent, or Firm—Blum, Kaplan, Friedman, Silberman & Beran

[57] ABSTRACT

Ester-azoxy compounds represented by the general formula:

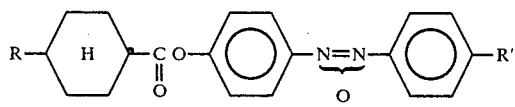

wherein R and R' are straight-chain alkyl groups having one to eight carbon atoms are provided. When added to a twisted nematic-type liquid crystal composition, the liquid crystal temperature range is increased.

30 Claims, 3 Drawing Figures

ESTER-AZOXY COMPOUNDS

BACKGROUND OF THE INVENTION

This invention relates to ester-azoxy compounds, and more particularly to ester-azoxy compounds having a nematic liquid crystal phase, which when added to a twisted nematic liquid crystal composition enlarge the liquid crystal temperature range, thereby improving liquid crystal display elements including the compositions.

It is generally known that nematic liquid crystal compounds are characteristic in that the electro-optical effect, such as light-scattering, double refraction and the like, changes greatly under the influence of an electric field. In view of these characteristics, nematic liquid crystals are used widely for liquid crystal display devices based on various display principles. The typical display principles include the twisted nematic display (TN-type) wherein the orientation of a nematic liquid crystal having a twisted configuration is controlled by application of an electric field across the crystal; the guest-host display (GH-type) wherein a guest-host effect is obtained by adding a dichroic dye to a TN-type display; and a phase transition display element wherein an optically active material is added to the liquid crystal and the spiral molecular arrangement is utilized.

The particular characteristics required of a liquid crystal material in order to be utilized in the above-mentioned display principles differ from each other. However, several conditions are required for all of them. First, the material must be stable chemically, and second it must be in the nematic state over a wide range of temperatures, encompassing room temperature.

Up to the present time, a single compound satisfying all of the above-mentioned conditions required for a liquid crystal display material has not been developed. Therefore, in order to obtain the desired properties in a liquid crystal material, various liquid crystal compositions which are mixtures of the various types of liquid crystal compounds have been utilized.

In order to provide a twisted nematic-type liquid crystal display (TN-LCD) having a large surface area, dynamic driving is required. Thus, liquid crystal compositions having improved dynamic characteristics are required. Particularly, the most significant property for improving dynamic driving is to provide a dynamic characteristic, for example the voltage-contrast characteristic. In other words, it is necessary to make the $\beta$ value closer to 1; $\Delta = V_{90}/V_{10}$.

In the case of dynamic driving of a TN-LCD, the liquid crystal materials are severely limited in their dynamic characteristics, liquid crystal temperature range and stability. Conventional liquid crystal materials do not satisfy all of these limitations. For example, azoxybenzene derivatives while superior in dynamic characteristics to other liquid crystal materials suffer from shortcoming of light resistance. Most of the other materials which are utilized as a base material in a liquid crystal composition are not fully satisfactory in that the liquid temperature range is small. In order to avoid these problems, a material having a high clear point is added, but this causes a decrease in the dynamic characteristic of the material.

Accordingly, it is desirable to provide a compound which when added to the liquid crystal composition as a dopant or when used as a base of a liquid crystal material or dynamic driving of a TN-LCD will improve the dynamic characteristics thereof and increase the liquid crystal temperature range.

SUMMARY OF THE INVENTION

Generally speaking, in accordance with the invention, P-(trans-4-alkylcyclohexylcarbonyloxy)-P'-alkylazoxybenzene compounds represented by the general formula:

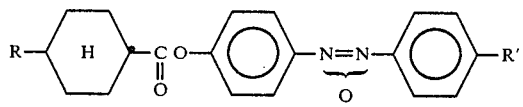

wherein R and R' are straight-chain alkyl groups having one to eight carbon atoms are provided. Preferably, the ester-azoxy compounds represented by the above formula are those wherein R is a straight-chain alkyl group having two to seven carbon atoms and R' is a straight-chain alkyl group having one to five carbon atoms.

The ester-azoxy compounds are prepared by converting P-alkylaniline into the hydrochloride which is diazotizated with an equivalent amount of sodium nitrite. The diazonium salt is coupled with phenol in 10% sodium hydroxide to yield P-alkyl-P'-hydroxyazobenzene. Trans-4-alkylcyclohexylcarboxylic acid is coupled with thionyl chloride to yield trans-4-alkylcyclohexylcarbonyl chloride. The P-alkyl-P'-hydroxyazobenzene and the trans-4-alkylcyclohexylcarbonyl chloride are esterified to provide P-(trans-4-alkylcyclohexylcarbonyloxy)-P'-alkylazobenzene which is oxidized with 35% hydrogen peroxide to yield P-(trans-4-alkylcyclohexylcarbonyloxy)-P'-alkylazoxybenzene.

Accordingly, it is an object of the invention to provide novel ester-azoxy compounds.

It is another object of the invention to provide P-(trans-4-alkylcyclohexylcarbonyloxy)-P'-alkylazoxybenzene compounds.

It is a further object of the invention to provide ester-azoxy compounds suitable for addition to twisted nematic liquid crystal compositions for improving the characteristics of the compositions.

Still another object of the invention is to provide a method for preparing the novel ester-azoxy compounds of the invention.

Still a further object of the invention is to provide improved nematic liquid crystal compositions including the novel ester-azoxy compounds in accordance with the invention.

Yet another object of the invention is to provide an improved liquid crystal display utilizing liquid crystal compositions including a novel ester-azoxy compounds in accordance with the invention.

Still other objects and advantages of the invention will in part be obvious and in part be apparent from the specification.

The invention accordingly comprises the compound and composition including the compound possessing the features, properties, and the relation of the constituents, the apparatus embodying features of construction characteristics, properties and relation of elements and the several steps and the relation of one or more of such steps with respect to each of the others which are exemplified in the following detailed disclosure, and the scope of the invention will be indicated in the claims.

BRIEF DESCRIPTION OF THE DRAWINGS

For a fuller understanding of the invention, reference is had to the following description taken in connection with the accompanying drawings, in which.

DESCRIPTION OF THE PREFERRED EMBODIMENTS

Figure 1:
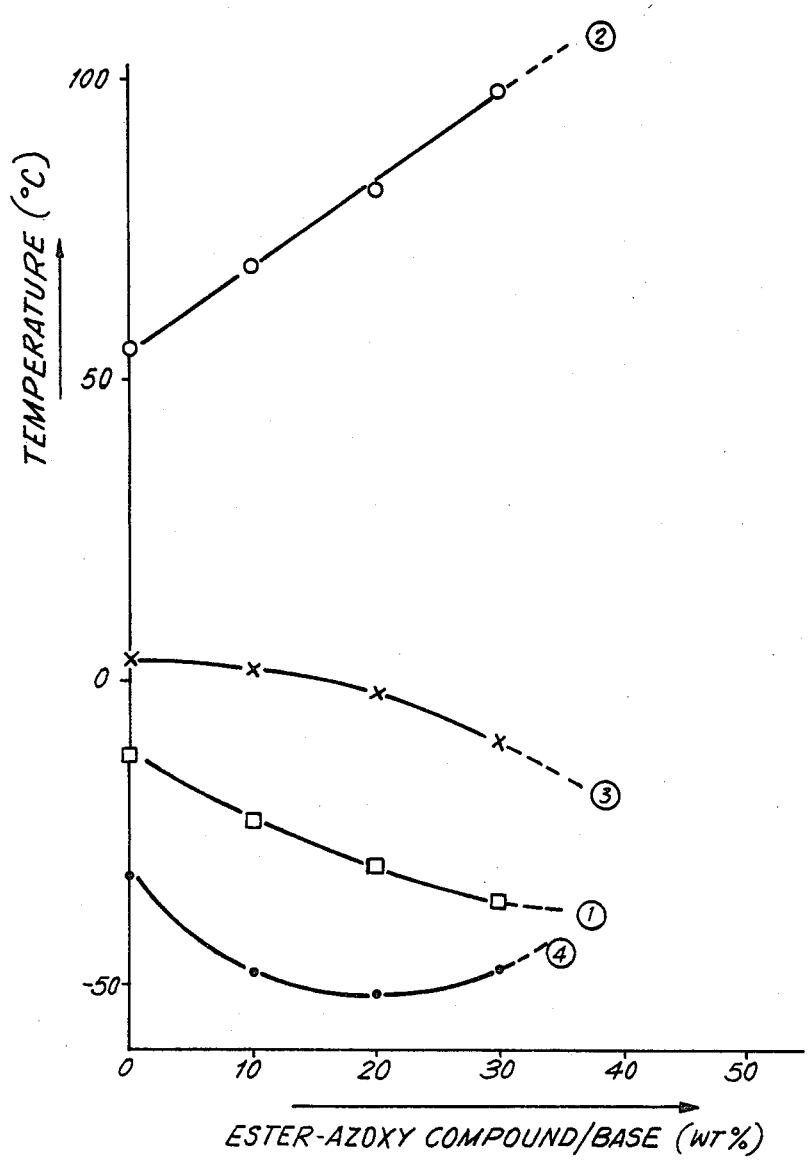
FIG. 1 is a graph illustrating the transition points of liquid crystal compositions including the novel ester-azoxy compounds prepared in accordance with the invention.

The novel ester-azoxy compound prepared in accordance with the invention are P-(trans-4-alkylcyclohexylcarbonyloxy)-P'-alkylazoxybenzene compounds represented by the general formula:

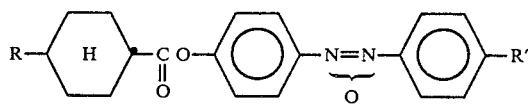

wherein R and R' are straight-chain alkyl groups having from one to eight carbon atoms. Preferably, the ester-azoxy compounds are those wherein R is a straight-chain alkyl group having two to seven carbon atoms and R' is a straight-chain alkyl group having from one to five carbon atoms.

The ester-azoxy compounds in accordance with the invention may be prepared in accordance with the following manufacturing process:

Step 1:

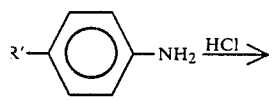

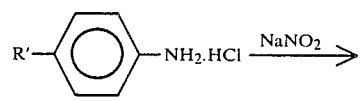

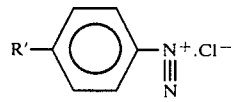

P-alkylaniline (which is commercially available) is converted into its hydrochloride by reaction with 5N hydrochloric acid. The hydroxhloride is diazotizated by an equivalent amount of sodium nitrite to yield the diazonium salt.

Step 2:

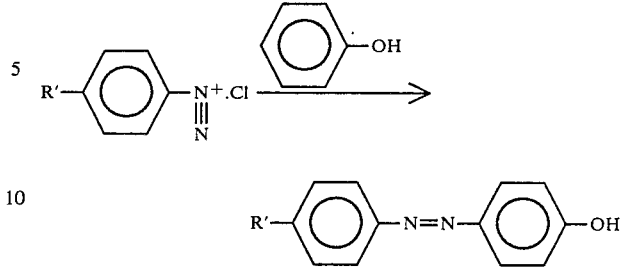

The diazonium salt prepared in Step 1 is coupled with phenol in a 10% sodium hydroxide solution to yield P-alkyl-P'-hydroxyazobenzene.

Step 3:

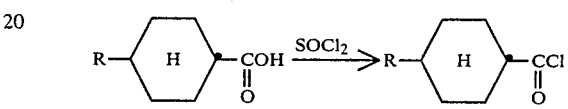

Trans-4-alkylcyclohexylcarboxylic acid (which is commercially available) is reacted with thionyl chloride to yield trans-4-alkylcyclohexylcarbonyl chloride.

Step 4:

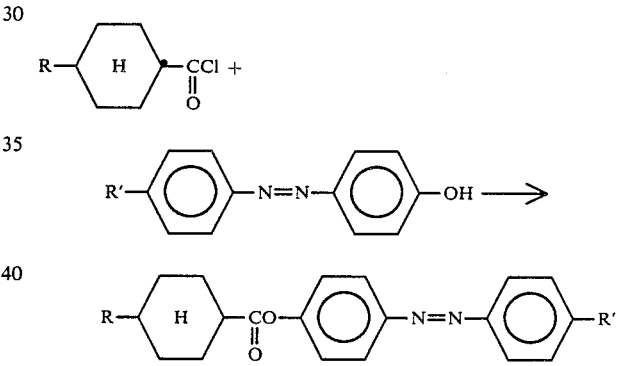

The P-alkyl-P'-hydroxyazobenzene prepared in Step 2 and the trans-4-alkylcyclohexylcarbonyl chloride prepared in Step 3 are esterified to yield P-(trans-4-alkylcyclohexylcarbonyloxy)-P'-alkylazobenzene.

Step 5:

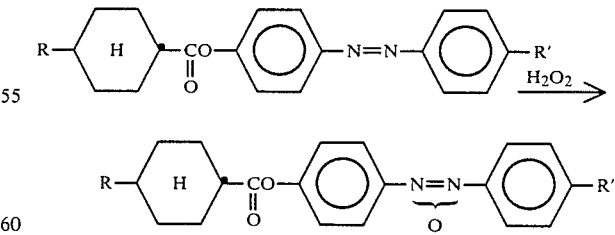

The P-(trans-4-alkylcyclohexylcarbonyloxy)-P'-alkylazobenzene prepared in Step 4 is oxidized by a 35% hydrogen peroxide solution to yield P-(trans-4-alkylcyclohexylcarbonyloxy)-P'-alkylazoxybenzene.

The ester-azoxy compound prepared in accordance with the above process have a nematic liquid crystal phase temperature range from about 70° to 230° C. In view of this, it is difficult to form a low temperature liquid crystal composition which will provide a nematic liquid crystal phase at temperatures lower than room temperature. However, it is relatively easy to expand the temperature range of liquid crystal compositions by the addition of existing liquid crystal compounds or liquid crystal compositions.

When the ester-azoxy compounds prepared in accordance with the invention are utilized in liquid crystal compositions, the clearing point of the composition is raised. In addition, the ester-azoxy compounds, in view their structure, provide characteristics which fall between the following well known groups of liquid crystal compositions identified as Groups (a) and Group (b) so that the electro-optical characteristics and stability of the compositions are assured.

Group (a): Trans-4-alkylcyclohexanecarboxylicacid-4'-alkoxyphenyl ester represented by the general formula:

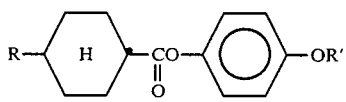

Group (b): P-P'-dialkylazoxybenzene represented by the general formula:

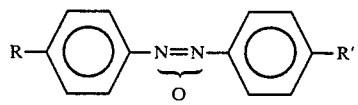

The method of preparing the ester-azoxy compounds in accordance with the invention and the application thereof are described in further detail in the following examples. These examples are set forth by way of illustration and not intended in a limiting sense.

EXAMPLE 1

P-(trans-4-pentylcyclohexylcarbonyloxy)-P'-pentylazoxybenzene was prepared as follows:

Step 1. 16.3 g of P-pentylaniline was dissolved in 25 ml of 36% hydrochloric acid by heating and the prepared solution was cooled to 0° to 5° C. A solution of 7.6 g of sodium nitrite in 20 ml of water was slowly added to the above-prepared solution by drops and the resulting solution was continuously mixed to yield the diazonium salt.

Step 2. A solution of 9.4 g of phenol and 10% sodium hydroxide prepared in advance by stirring, said diazonium salt solution was dropped into the solution of 9.4 g of phenol/10% caustic soda little by little and then the two solutions were coupled. After the coupling reaction, the resulting solution was poured in an adequate amount of dilute hydrochloric acid to form a precipitate. The precipitate was filtrated and washed with water several times and then hexane which easily removed remaining impurities. The washed precipitate was recrystallized in toluene to yield pure P-pentyl-P'-hydroxyazobenzene.

Step 3. 5.58 g Of trans-4-pentylcyclohexylcarboxylic acid was heated with 20 ml of thionyl chloride under reflux conditions. After the reaction was completed, the excess of thionyl chloride was removed completely under reduced pressure and the product residue obtained was distilled under reduced pressure. Trans-4-pentylcyclohexylcarbonyl chloride having a boiling point of 103° to 105° C./0.5 mmHg was obtained.

Step 4. 2.5 g Of P-pentyl-P'-hydroxyazobenzene prepared in Step 2 and 1.9 ml of triethylamine were dissolved in 20 ml of ethyl ether and cooled to 0° to 5° C. 10 ml Of an ethyl ether solution having 2 g of the trans-4-penthylcyclohexylcarbonyl chloride prepared in Step 3 dissolved therein was added to the first solution gradually with complete mixing. The resulting mixture was heated under reflux conditions for one hour. After the reaction was completed an adequate amount of water was added thereto and triethylamine hydrochloride was dissolved therein.

The resulting solution was placed in a separating funnel and the ether layer was washed with water, 5% sodium hydroxide solution and 5N hydrochloric acid. The resulting ether solution was dehydrated by using sodium sulphate anhydride, and ether was removed by distilation. The remaining product residue was recrystallized in ethanol. The compound produced by this step is P-(trans-4-pentylcyclohexylcarbonyloxy)-P'-pentylazobenzene.

Step 5. 33 g of the P-(trans-4-pentylcyclohexylcarbonyloxy)-P'-pentylazobenzene prepared in Step 4, 100 ml of glacial acetic acid and 2.9 ml of 35% hydrogen peroxide were mixed and heated to 75° to 80° C. for eight hours. After the reaction was completed, the solution was cooled to room temperature. The product was recrystallized by cooling, filtered and further recrystallized again in ethanol and then hexane. The resulting compound produced is P-(trans-4-pentylcyclohexylcarbonyloxy)-P'-pentylazoxybenzene which is an ester-azoxy compound in accordance with this invention.

EXAMPLES 2–21

Following the procedure outlined in Example 1, the following ester-azoxy compounds listed below were produced by using the appropriate P-alkylaniline and trans-4-alkylcyclohexylcarboxylic acid.

| Example | Ester-azoxy Compound Prepared |
| --- | --- |
| Example 2 | P—(trans-4-ethylcyclohexlycarbonyloxy)-P'—methylazoxybenzene |
| Example 3 | P—(trans-4-propylcyclohexylcarbonyloxy)-P'—methylazoxybenzene |
| Example 4 | P—(trans-4-butylcyclohexylcarbonyloxy)-P'—methylazoxybenzene |
| Example 5 | P—(trans-4-ethylcyclohexylcarbonyloxy)-P'—ethylazoxybenzene |
| Example 6 | P—(trans-4-propylcyclohexylcarbonyloxy)-P'—ethylazoxybenzene |
| Example 7 | P—(trans-4-butylcyclohexylcarbonyloxy)-P'—ethylazoxybenzene |
| Example 8 | P—(trans-4-pentylcyclohexylcarbonyloxy)-P'—ethylazoxybenzene |
| Example 9 | P—(trans-4-ethylcyclohexylcarbonyloxy)-P'—propylazoxybenzene |
| Example 10 | P—(trans-4-propylcyclohexylcarbonyloxy)-P'—propylazoxybenzene |
| Example 11 | P—(trans-4-butylcyclohexylcarbonyloxy)-P'—propylazoxybenzene |
| Example 12 | P—(trans-4-pentylcyclohexylcarbonyloxy)-P'—propylazoxybenzene |
| Example 13 | P—(trans-4-hexylcyclohexylcarbonyloxy)-P'—propylazoxybenzene |
| Example 14 | P—(trans-4-heptylcyclohexylcarbonyloxy)-P'—propylazoxybenzene |
| Example 15 | P—(trans-4-propylcyclohexylcarbonyloxy)-P'—butylazoxybenzene |
| Example 16 | P—(trans-4-butylcyclohexylcarbonyloxy)-P'—butylazoxybenzene |
| Example 17 | P—(trans-4-pentylcyclohexylcarbonyloxy)-P'—butylazoxybenzene |

-continued

| Example | Ester-azoxy Compound Prepared |
|---|---|
| Example 18 | P—(trans-4-hexylcyclohexylcarbonyloxy)-P'—butylazoxybenzene |
| Example 19 | P—(trans-4-heptylcyclohexylcarbonyloxy)-P'—butylazoxybenzene |
| Example 20 | P—(trans-4-propylcyclohexylcarbonyloxy)-P'—pentylazoxybenzene |
| Example 21 | P—(trans-4-butylcyclohexylcarbonyloxy)-P'—pentylkazoxybenzene |

The following Table 1 shows the transition points of compounds prepared in Examples 1–21. In Table 1, C-N represents the melting point, N-I represents the nematic-isotropic transition and N-S represents the nematic-smectic transition.

TABLE 1

| Example | Compound | Transition Point (°C.) |
|---|---|---|
| 1 | C$_5$H$_{11}$—[H]—CO—O—⟨⟩—N=N(O)—⟨⟩—C$_5$H$_{11}$ | C →62→ N ←238← I; ←S← |
| 2 | C$_2$H$_5$—[H]—CO—O—⟨⟩—N=N(O)—⟨⟩—CH$_3$ | C →86→ N ←234← I; ←64←S←62← |
| 3 | C$_3$H$_7$—[H]—CO—O—⟨⟩—N=N(O)—⟨⟩—CH$_3$ | C →81→ N ←254← I; ←59←S←57← |
| 4 | C$_4$H$_9$—[H]—CO—O—⟨⟩—N=N(O)—⟨⟩—CH$_3$ | C →86→ N ←246← I; ←61←S←66← |
| 5 | C$_2$H$_5$—[H]—CO—O—⟨⟩—N=N(O)—⟨⟩—C$_2$H$_5$ | C →83→ N ←221← I; ←65←S←66← |
| 6 | C$_3$H$_7$—[H]—CO—O—⟨⟩—N=N(O)—⟨⟩—C$_2$H$_5$ | C →83→ N ←241← I; ←58←S←60← |
| 7 | C$_4$H$_9$—[H]—CO—O—⟨⟩—N=N(O)—⟨⟩—C$_2$H$_5$ | C →81→ N ←233← I; ←54←S←67← |
| 8 | C$_5$H$_{11}$—[H]—CO—O—⟨⟩—N=N(O)—⟨⟩—C$_2$H$_5$ | C →74→ N ←234← I; ←30←S←64← |
| 9 | C$_2$H$_5$—[H]—CO—O—⟨⟩—N=N(O)—⟨⟩—C$_3$H$_7$ | C →72→ N ←224← I; ←52←S←62← |
| 10 | C$_3$H$_7$—[H]—CO—O—⟨⟩—N=N(O)—⟨⟩—C$_3$H$_7$ | C →80→ N ←246← I; ←S← |
| 11 | C$_4$H$_9$—[H]—CO—O—⟨⟩—N=N(O)—⟨⟩—C$_3$H$_7$ | C →79→ N ←239← I; ←S← |

TABLE 1-continued

| Example | Compound | Transition Point (°C.) |
|---|---|---|
| 12 | $C_5H_{11}$—[H]—COO—⟨⟩—N=N(O)—⟨⟩—$C_3H_7$ | C ⇌ 76 ⇌ N ⇌ 236 ⇌ I (S below) |
| 13 | $C_6H_{13}$—[H]—COO—⟨⟩—N=N(O)—⟨⟩—$C_3H_7$ | C ⇌ 82 ⇌ N ⇌ 226 ⇌ I (S below) |
| 14 | $C_7H_{15}$—[H]—COO—⟨⟩—N=N(O)—⟨⟩—$C_3H_7$ | C ⇌ 88 ⇌ N ⇌ 222 ⇌ I; S ⇌67, ⇌75 |
| 15 | $C_3H_7$—[H]—COO—⟨⟩—N=N(O)—⟨⟩—$C_4H_9$ | C ⇌ 63 ⇌ N ⇌ 233 ⇌ I (S below) |
| 16 | $C_4H_9$—[H]—COO—⟨⟩—N=N(O)—⟨⟩—$C_4H_9$ | C ⇌ 67 ⇌ N ⇌ 227 ⇌ I (S below) |
| 17 | $C_5H_{11}$—[H]—COO—⟨⟩—N=N(O)—⟨⟩—$C_4H_9$ | C ⇌ 69 ⇌ N ⇌ 224 ⇌ I (S below) |
| 18 | $C_6H_{13}$—[H]—COO—⟨⟩—N=N(O)—⟨⟩—$C_4H_9$ | C ⇌ 69 ⇌ N ⇌ 217 ⇌ I (S below) |
| 19 | $C_7H_{15}$—[H]—COO—⟨⟩—N=N(O)—⟨⟩—$C_4H_9$ | C ⇌ 63 ⇌ N ⇌ 212 ⇌ I (S below) |
| 20 | $C_3H_7$—[H]—COO—⟨⟩—N=N(O)—⟨⟩—$C_5H_{11}$ | C ⇌ 80 ⇌ N ⇌ 245 ⇌ I; S ⇌51, ⇌62 |
| 21 | $C_4H_9$—[H]—COO—⟨⟩—N=N(O)—⟨⟩—$C_5H_{11}$ | C ⇌ 79 ⇌ N ⇌ 236 ⇌ I; S ⇌32, ⇌52 |

EXAMPLE 22

Several liquid crystal compositions including various proportions of ester-azoxy compounds prepared in accordance with the invention were prepared as indicated on the columns A, B, C and D. In each case, the ester-azoxy compounds were present in amounts varying from 0, 10, 20 and 30 weight percent, respectively.

TABLE 2

| | A (0% Ester-Azoxy) | B (10% Ester-Azoxy) | C (20% Ester Azoxy) | D (30% Ester Azoxy) |
|---|---|---|---|---|
| $C_5H_{11}$—⟨⟩—N=N(O)—⟨⟩—$C_5H_{11}$ | 52.7 | 47.4 | 42.1 | 36.8 |

TABLE 2-continued

| | A (0% Ester-Azoxy) | B (10% Ester-Azoxy) | C (20% Ester Azoxy) | D (30% Ester Azoxy) |
|---|---|---|---|---|
| $C_6H_{13}$—⟨O⟩—N=N(O)—⟨O⟩—$C_6H_{13}$ | 35.0 | 31.5 | 28.0 | 24.5 |
| $C_2H_5$—⟨O⟩—COO—⟨O⟩—CN | 10.0 (100) | 9.0 (90) | 8.0 (80) | 7.0 (70) |
| $C_4H_9$—⟨O⟩—COO—⟨O⟩—CN | 2.0 | 1.8 | 1.6 | 1.4 |
| $CH_3CH_2\overset{*}{C}HCH_2O$—⟨O⟩—⟨O⟩—CN (with $CH_3$) | 0.3 | 0.3 | 0.3 | 0.3 |
| $C_3H_7$—⟨H⟩—COO—⟨O⟩—N=N(O)—⟨O⟩—$C_3H_7$ | 0 (0) | 6.0 (10) | 12.0 (20) | 18.0 (30) |
| $C_5H_{11}$—⟨H⟩—COO—⟨O⟩—N=N(O)—⟨O⟩—$C_3H_7$ | 0 | 4.0 | 8.0 | 12.0 |

The transition points of each of the liquid crystal compositions designated A, B, C and D were measured by using a differential thermal analyzer. The results of the measurements are shown in FIG. 1. In FIG. 1, the abscissa represents the amount of ester-azoxy compound in accordance with the invention present in the liquid crystal composition and corresponds to compositions A, B, C and D in Table 2.

Referring to FIG. 1, the curve designated 1 represents the melting point temperature of each liquid crystal composition A, B, C and D after the compositions have been dissolved and re-solidified. The curve designated 2 shows the clear point temperatures, or the point at which each composition is transformed from the nematic phase to the isotropic liquid. The curve designated 3 shows the transition point temperature when the compositions are transformed from the nematic phase to the smectic phase. The curve designated 4 shows the transition point temperatures when each composition is transformed from the smectic phase to a crystal.

As is shown clearly in FIG. 1, when the amount of the ester-azoxy compound prepared in accordance with the invention is increased in the composition, the nematic liquid crystal temperature range clearly is increased. Additionally, the amount of expansion of the nematic phase is quite remarkable and unexpected.

EXAMPLE 23

Figure 2:
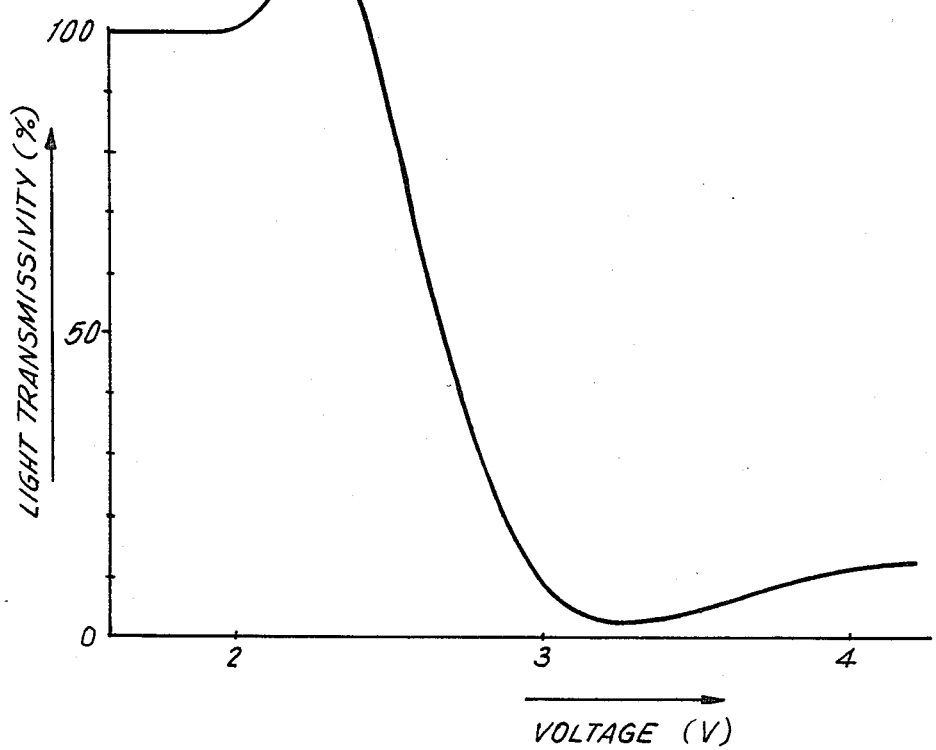
FIG. 2 is a graph illustrating the voltage-contrast characteristic of liquid crystal compositions including the novel ester-azoxy compounds in accordance with the invention.

The composition designated B in Table 2 was placed in a twisted nematic-type liquid cell having a thickness of 7 microns. The voltage-contrast characteristics of the cell were investigated and are set forth in FIG. 2. When comparing the results of the cell as shown in FIG. 2 to conventional positions constructed for 3 V driving, the composition B prepared in accordance with the invention is certainly not inferior to conventional devices and is also quite suitable for commercial use.

Figure 3:
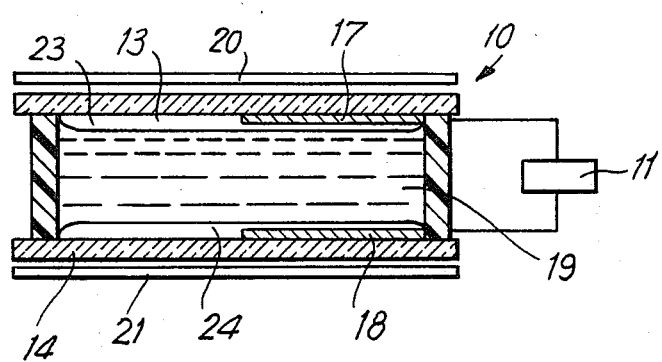
FIG. 3 is a cross-sectional view of a liquid crystal display cell utilizing a liquid crystal composition including the novel ester-azoxy compounds in accordance with the invention.

As described above, the ester-azoxy compounds disclosed herein can be used as one of the liquid crystal materials for liquid crystal display cells. A typical liquid crystal display device 10 is shown in FIG. 3 and includes a drive circuit 11 for applying drive signals to liquid crystal cell 12. Cell 12 includes upper substrate 13 and a lower substrate 14 spaced apart by a spacer 16 and each having electrodes 17 and 18 disposed on the interior surfaces thereof, respectively. Cell 12 also includes an upper polarizer 20 and a lower polarizer 21 in a transmissive device illustrated and may include a reflector on the lower polarizer 21. A liquid crystal composition 19 including an ester-azoxy compound prepared in accordance with the invention is disposed in the space between substrate 13 and 14. The interior surfaces of substrates 13 and 14 and electrodes 17 and 18 may be covered with liquid crystal molecule orientation layers 22 and 23.

Signals are selectively applied to electrodes 17 and 18. The voltage drop between cooperating opposed electrodes cause that portion of the liquid crystal composition therebetween to be rendered visually distinguishable from the remainder of the liquid crystal composition in response to polarized light entering cell 12. At least one of electrodes 17 and 18 is transparent.

When liquid crystal display device 10 includes an ester-azoxy compound admixed in the liquid crystal composition, the nematic range of the liquid crystal material is substantially expanded without decreasing the desirable characteristics of the liquid crystal composition.

It will thus be seen that the objects set forth above, among those made apparent from the preceding description are efficiently attained and, since certain changes may be made in the compound, composition, construction and methods set forth without departing from the spirit and scope of the invention, it is intended that all matter contained in the above description and shown in the accompanying drawing shall be interpreted as illustrative and not in a limiting sense.

It is also to be understood that the following claims are intended to cover all of the generic and specific features of the invention herein described and all statements of the scope of the invention which, as a matter of language, might be said to fall therebetween.

Particularly it is to be understood that in said claims, ingredients or compounds recited in the singular are intended to include compatible mixtures of such ingredients whenever the sense permits.

What is claimed is:

1. P-(trans-4-alkylcyclohexylcarbonyloxy)-P'-alkylazoxybenzene represented by the general formula:

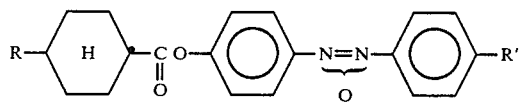

wherein R and R' are straight-chain alkyl groups having one to eight carbon atoms.

2. The P-(trans-4-alkylcyclohexylcarbonyloxy)-P'-alkylazoxybenzene of claim 1, wherein the R group has two to seven carbon groups and the R' group has one to five carbon atoms.

3. The P-(trans-4-alkylcyclohexylcarbonyloxy)-P'-alkylazoxybenzene of claim 1, wherein the R and R' groups are pentyl to define P-(trans-4-pentylcyclohexylcarbonyloxy)-P'-pentylazoxybenzene having the formula

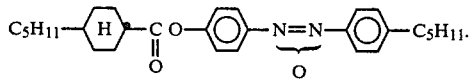

4. The P-(trans-4-alkylcyclohexylcarbonyloxy)-P'-alkylazoxybenzene of claim 1, wherein R is ethyl and R' is methyl to define P-(trans-4-ethylcyclohexylcarbonyloxy)-P'-methylazoxybenzene having the formula

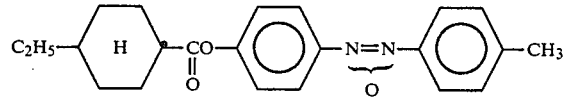

5. The P-(trans-4-alkylcyclohexylcarbonyloxy)-P'-alkylazoxybenzene of claim 1, wherein R is propyl and R' is methyl to define P-(trans-4-propylcyclohexylcarbonyloxy)-P'-methylazoxybenzene having the formula

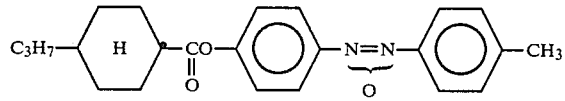

6. The P-(trans-4-alkylcyclohexylcarbonyloxy)-P'-alkylazoxybenzene of claim 1, wherein R is butyl and R' is methyl to define P-(trans-4-butylcyclohexylcarbonyloxy)-P'-ethylazoxybenzene having the formula

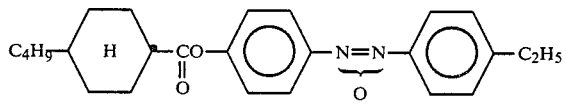

7. The P-(trans-4-alkylcyclohexylcarbonyloxy)-P'-alkylazoxybenzene of claim 1, wherein the R and R' groups are ethyl to define P-(trans-4-ethylcyclohexylcarbonyloxy)-P'-ethylazoxybenzene having the formula

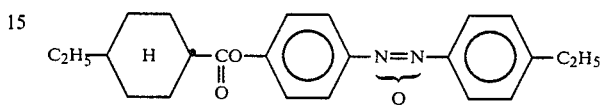

8. The P-(trans-4-alkylcyclohexylcarbonyloxy)-P'-alkylazoxybenzene of claim 1, wherein R is propyl and R' is ethyl to define P-(trans-4-propylcyclohexylcarbonyloxy)-P'-ethylazoxybenzene having the formula

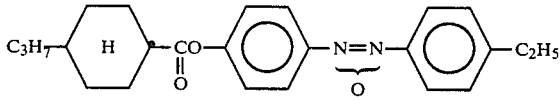

9. The P-(trans-4-alkylcyclohexylcarbonyloxy)-P'-alkylazoxybenzene of claim 1, wherein R is butyl and R' is ethyl to define P-(trans-4-butylcyclohexylcarbonyloxy)-P'-ethylazoxybenzene having the formula

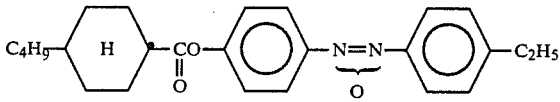

10. The P-(trans-4-alkylcyclohexylcarbonyloxy)-P'-alkylazoxybenzene of claim 1, wherein R is pentyl and R' is ethyl to define P-(trans-4-pentylcyclohexylcarbonyloxy)-P'-ethylazoxybenzene having the formula

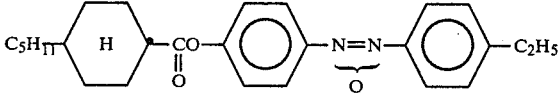

11. The P-(trans-4-alkylcyclohexylcarbonyloxy)-P'-alkylazoxybenzene of claim 1, wherein R is ethyl and R' is propyl to define P-(trans-4-ethylcyclohexylcarbonyloxy)-P'-propylazoxybenzene having the formula

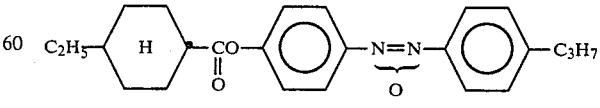

12. The P-(trans-4-alkylcyclohexylcarbonyloxy)-P'-alkylazoxybenzene of claim 1, wherein the R and R' groups are propyl to define P-(trans-4-propylcyclohexylcarbonyloxy)-P'-propylazoxybenzene having the formula

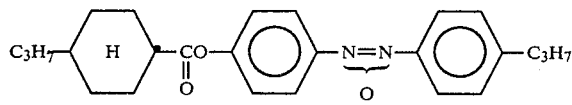

13. The P-(trans-4-alkylcyclohexylcarbonyloxy)-P'-alkylazoxybenzene of claim 1, wherein R is butyl and R' is propyl to define P-(trans-4-butylcyclohexylcarbonyloxy)-P'-propylazoxybenzene having the formula

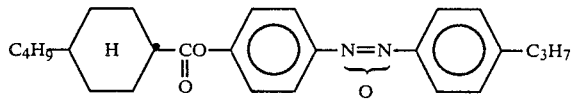

14. The P-(trans-4-alkylcyclohexylcarbonyloxy)-P'-alkylazoxybenzene of claim 1, wherein R is pentyl and R' is propyl to define P-(trans-4-pentylcyclohexylcarbonyloxy)-P'-propylazoxybenzene having the formula

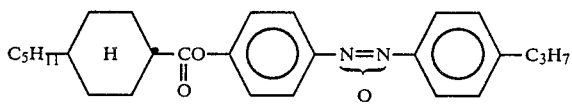

15. The P-(trans-4-alkylcyclohexylcarbonyloxy)-P'-alkylazoxybenzene of claim 1, wherein R is hexyl and R' is propyl to define P'(trans-4-hexylcyclohexylcarbonyloxy)-P'-propylazoxybenzene having the formula

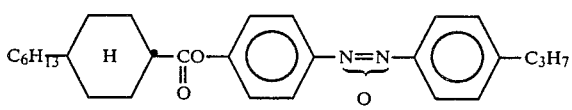

16. The P-(trans-4-alkylcyclohexylcarbonyloxy)-P'-alkylazoxybenzene of claim 1, wherein R is heptyl and R' is propyl to define P-(trans-4-heptylcyclohexylcarbonyloxy)-P'-propylazoxybenzene having the formula

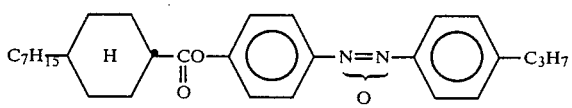

17. The P-(trans-4-alkylcyclohexylcarbonyloxy)-P'-alkylazoxybenzene of claim 1, wherein R is propyl and R' is butyl to define P-(trans-4-propylcyclohexylcarbonyloxy)-P'-butylazoxybenzene having the formula

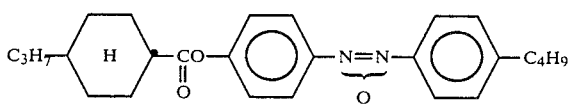

18. The P-(trans-4-alkylcyclohexylcarbonyloxy)-P'-alkylazoxybenzene of claim 1, wherein the R and R' groups are butyl to define P-(trans-4-butylcyclohexylcarbonyloxy)-P'-butylazoxybenzene having the formula

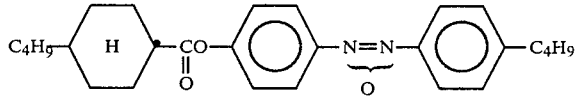

19. The P-(trans-4-alkylcyclohexylcarbonyloxy)-P'-alkylazoxybenzene of claim 1, wherein R is pentyl and R' is butyl to define P-(trans-4-pentylcyclohexylcarbonyloxy)-P'-butylazoxybenzene having the formula

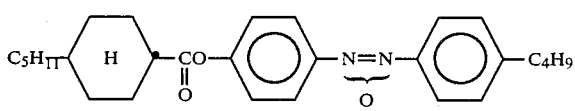

20. The P-(trans-4-alkylcyclohexylcarbonyloxy)-P'-alkylazoxybenzene of claim 1, wherein R is hexyl and R' is butyl to define P-(trans-4-hexylcyclohexylcarbonyloxy)-P'-butylazoxybenzene having the formula

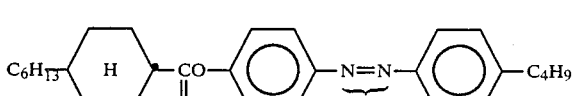

21. The P-(trans-4-alkylcyclohexylcarbonyloxy)-P'-alkylazoxybenzene of claim 1, wherein R is heptyl and R' is butyl to define P-(trans-4-heptylcyclohexylcarbonyloxy)-P'-butylazoxybenzene having the formula

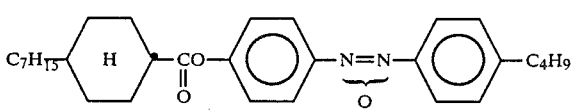

22. The P-(trans-4-alkylcyclohexylcarbonyloxy)-P'-alkylazoxybenzene of claim 1, wherein R is propyl and R' is pentyl to define P-(trans-4-propylcyclohexylcarbonyloxy)-P'-pentylazoxybenzene having the formula

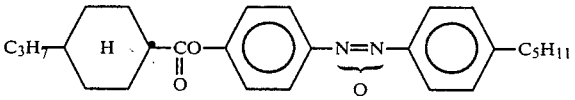

23. The P-(trans-4-alkylcyclohexylcarbonyloxy)-P'-alkylazoxybenzene of claim 1, wherein R is butyl and R' is pentyl to define P-(trans-4-butylcyclohexylcarbonyloxy)-P'-pentylazoxybenzene having the formula

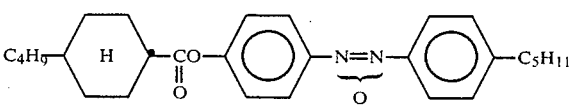

24. A liquid crystal mixture comprising P-(trans-4-alkylcyclohexylcarbonyloxy)-P'-alkylazoxybenzene having the general formula

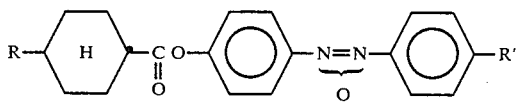

wherein R and R' are straight-chain alkyl groups having from one to eight carbon atoms.

25. The mixture of claim 24, wherein the R group has two to seven carbon atoms and the R' group has one to five carbon atoms.

26. The liquid crystal mixture of claim 24, wherein the P-(trans-4-alkylcyclohexylcarbonyloxy)-P'-alkylazoxybenzene is present in an amount ranging from at least an effective amount to increase the liquid crystal temperature range to about 30 weight percent.

27. The liquid crystal mixture of claim 24, wherein the liquid crystal mixture further includes at least one twisted nematic-type liquid crystal material.

28. The liquid crystal mixture of claim 27, wherein the twisted nematic liquid crystal material comprises azoxy-type liquid crystals, ester-type liquid crystals or mixtures thereof.

29. A liquid crystal display device, comprising two opposed substantially parallel substrates with liquid crystal electrodes selectively disposed on the interior surfaces thereof, a liquid crystal composition in the space between the substrates, circuit means for generating signals to be selectively applied to the liquid crystal electrodes for rendering the liquid crystal composition between the electrodes visually distinguishable from the remaining liquid crystal composition, the liquid crystal composition comprising at least one P-(trans-4-alkylcyclohexylcarbonyloxy)-P'-alkylazoxybenzene having the general formula

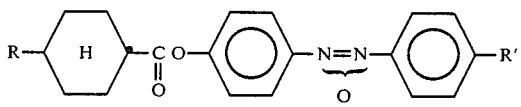

wherein R and R' are straight-chain alkyl groups having from one to eight carbon atoms.

30. The liquid crystal display device of claim 29, wherein the R group has from two to seven carbon atoms and the R' group has from one to five carbon atoms.

* * * * *